United States Patent [19]

Gallagher

[11] Patent Number: 4,987,082
[45] Date of Patent: Jan. 22, 1991

[54] CONTROL OF FOAM BUILD UP IN A FERMENTER

[75] Inventor: Stephen F. Gallagher, Maidstone, England

[73] Assignee: Shell Internationale Research, The Hague, Netherlands

[21] Appl. No.: 389,593

[22] Filed: Aug. 4, 1989

[30] Foreign Application Priority Data

Aug. 5, 1988 [GB] United Kingdom ............... 8818712

[51] Int. Cl.$^5$ ............................................. C12M 1/36
[52] U.S. Cl. .................................. 435/289; 435/291; 435/812; 307/118; 73/304 R
[58] Field of Search ............ 73/304 R, ; 307/118; 435/289, 291, 812

[56] References Cited

U.S. PATENT DOCUMENTS

| 3,036,736 | 5/1962 | Murphy et al. ............... 73/304 R |
| 3,119,266 | 1/1964 | Atkinson .................... 73/304 R |
| 3,373,351 | 3/1968 | Rak ........................... 73/304 |
| 3,461,722 | 8/1969 | Martens ...................... 73/304 R |
| 3,806,423 | 4/1974 | Karrenbauer et al. ......... 435/289 |
| 4,027,172 | 5/1977 | Hamelink . |
| 4,390,793 | 6/1983 | John . |
| 4,714,189 | 12/1987 | Tovey ......................... 73/304 R |
| 4,728,005 | 3/1988 | Jacobs et al. ................. 73/304 R |
| 4,739,786 | 4/1988 | Parkinson .................... 307/118 |
| 4,749,988 | 6/1988 | Berman et al. . |
| 4,752,564 | 6/1988 | Hopkins ....................... 435/812 |
| 4,757,252 | 7/1988 | Maltby et al. . |

FOREIGN PATENT DOCUMENTS

| 152644 | 8/1985 | European Pat. Off. . |
| 1470861 | 4/1977 | United Kingdom ......... 435/812 |
| 1497120 | 1/1978 | United Kingdom . |

Primary Examiner—Carroll B. Dority
Attorney, Agent, or Firm—Jones, Tullar & Cooper

[57] ABSTRACT

The use of a probe for the control of foam build up in a fermenter, which probe comprises a guard electrode (13), first and second insulators (14 and 15) separated by the guard electrode, a detecting electrode (12) separated from the guard electrode by the first insulator, and a plug (18) and socket (17) for connecting the probe to a power source, the second insulator being provided with fermenter mounting means in the form of a flange (16), a sensor comprising the aforementioned probe for use with an antifoam supply regulator, a foam control system and a method of controlling the build up of foam in a fermentation vessel.

9 Claims, 3 Drawing Sheets

CONTROL OF FOAM BUILD UP IN A FERMENTER

BACKGROUND OF THE INVENTION

The present invention relates to the use of a probe for the control of foam build up in a fermenter, to a sensor comprising the probe for use with an antifoam supply regulator in the control of foam build up in a fermenter, to such a foam control system, to a fermenter comprising the foam control system, and to a method of controlling foam build up in a fermenter.

During many microbiological fermentation processes foam is produced. Its presence is undesirable since it reduces the amount of oxygen reaching the broth during the fermentation and impedes the processing of the broth after the fermentation has been completed. Furthermore, if uncontrolled, it can block exit gas lines and eventually spill out of the fermenter.

Much attention has been devoted to the development of automatic control systems for the prevention of foam build up in fermenters. Such systems typically comprise a sensor which detects when foam has risen up to a predetermined level, and an antifoam dispenser which supplies an antifoam substance to the fermenter when the sensor detects the foam. Suitable antifoam substances include polypropylene glycol 2,000 and silicone based products, for example Dow Corning silicone RID emulsion.

One known and commercially available type of foam sensor comprises a probe having an electrode which, in use, is inserted through a wall or closure in the fermenter to the predetermined level and powered with a low voltage. When foam has risen up to touch the electrode, an electric current begins to flow through the foam and fermentation broth to earth. Thus the potential at the electrode drops, and this change in potential is exploited to activate an antifoam supply. However, it is found that such probes are unreliable over a long period of time. Thus foam control systems comprising this known type of probe tend to deliver increasingly excessive amounts of antifoam substance to the fermentation broth as the fermentation progresses.

The presence of excess antifoam substance in a fermentation broth is disadvantageous because it reduces the rate of inward diffusion of oxygen and makes downstream processing, particularly product recovery, difficult. Clearly, therefore, there is a need for a probe capable of being used in the control of foam produced during fermentation without resulting in unacceptably high levels of antifoam substance in the fermentation broth.

The specification of U.S. Pat. No. 3,119,266 (US-A-3,119,266) discloses a probe for detecting or measuring the level or quantity of liquid, powder, granular or aggregate materials in bins, tanks or other containers, which comprise first and second, or measuring conductive electrodes and a guard electrode which is driven in phase with the voltage derived between the measuring electrodes with a voltage of substantially the same magnitude as the measuring voltage.

The specification of U.S. Pat. No. 4,027,172 (US-A-4,027,172) discloses a modified version of the probe described in US-A-3,119,266, with particular emphasis placed on the use of the modified probe in detecting the presence or absence of boiler water in heating plant boilers. The features of the probes of both US-A-3,119,266 and US-A-4,027,172 are combined in the specification of U.S. Pat. No. 4,390,793, which discloses a multifunction electronic probe circuit for water level control.

SUMMARY OF THE INVENTION

Most surprisingly, it has now been found that the use of a probe comprising a guard electrode in the control of foam build up in microbial fermentation processes provides a foam sensor having a significantly greater reliability over prolonged periods of fermentation compared with the reliability of the known types of probe available commercially.

Accordingly, the present invention provides the use of a probe for the control of foam build up in a fermenter, which probe comprises a guard electrode, first and second insulators separated by the guard electrode, a detecting electrode separated from the guard electrode by the first insulator, means for independently connecting each of the electrodes to a power source, and vessel mounting means for positioning the detecting electrode at the predetermined level with the guard electrode insulated from the vessel by the second insulator. It has been found that, unlike known probes, the performance of a probe comprising a guard electrode, when used to control foam build up in a fermenter does not decline as the fermentation progresses.

The vessel mounting means preferably comprises a flange or neck on the second insulator. This flange or neck may be an integral part of the second insulator or may be a removable part such as a sleeve.

Since the probe is primarily intended for use in a fermenter, it is preferably composed of materials that are capable of withstanding serialization in an autoclave. Thus, the electrodes may, for example, be composed of stainless steel. The insulators may, for example, be composed of polyetheretherketone, fibreglass loaded polytetrafluoroethylene, glass or polyoxymethylene, with polyetheretherketone being preferred.

Conveniently the means for independently connecting each of the electrodes to a power source comprises a plug, a socket and wires connecting the electrodes to the socket.

According to another aspect the invention provides a sensor for use with an antifoam supply regulator in the control of foam build up in a fermenter, which comprises a probe as described above and an electric circuit which comprises means for providing the detecting electrode with alternating potential, means for controlling the potential at the guard electrode so as to maintain a zero potential difference between the two electrodes, and means for providing the antifoam supply regulator with an electric signal when foam causes a change in potential at the detecting electrode. The electric circuit may optionally also comprise a timer which enables the electric signal to be provided for a preset time. This is particularly advantageous since the antifoam substance does not take effect immediately and it is important to supply only the minimum amount of antifoam substance necessary to control the foam.

According to a further aspect, the invention provides a foam control system for use with a fermenter, which comprises an apparatus as defined above and an antifoam supply regulator.

In the foam control system the antifoam supply regulator preferably comprises a pump or valve.

The invention also provides a fermenter comprising a foam control system as defined above.

According to another aspect the invention provides a method of controlling the build up of foam in a fermentation vessel, which comprises supplying power to a detecting electrode positioned at a predetermined level in the fermentation vessel;

controlling the potential of a guard electrode positioned between the detecting electrode and the fermentation vessel such that a zero potential difference is maintained between the two electrodes; and supplying a controlled amount of an antifoam substance into the fermentation vessel whenever foam causes a change in potential at the detecting electrode.

BRIEF DESCRIPTION OF THE DRAWINGS

The invention will now be described in more detail by way of example with reference to the accompanying drawings, in which.

DESCRIPTION OF THE PREFERRED EMBODIMENT

Figure 1:
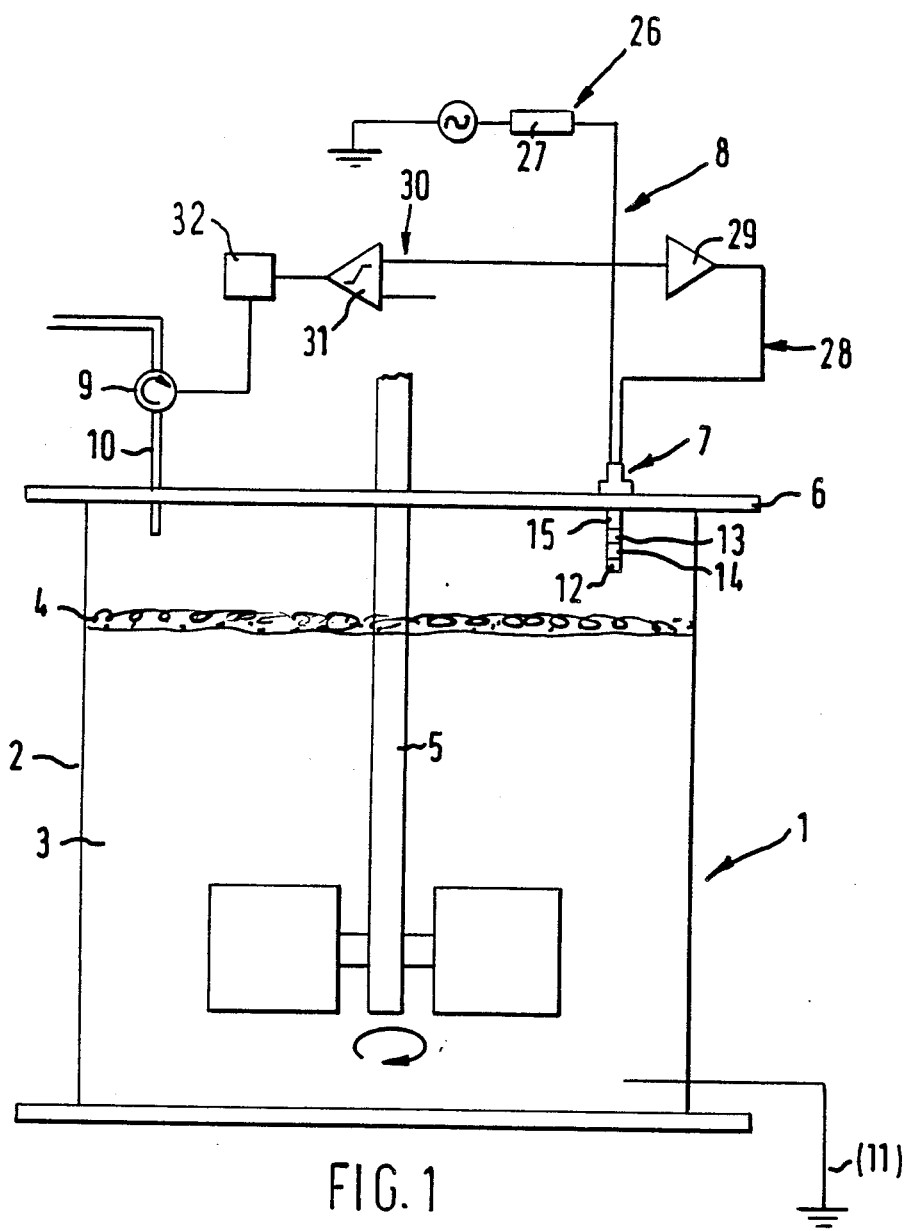
FIG. 1 shows a schematic representation of a fermenter which includes a probe for use in accordance with the present invention.

FIG. 1 shows a fermenter (1) comprising a stainless steel fermentation vessel (2) containing a fermentation broth (3). The broth has a covering layer of foam (4). The fermentation vessel is equipped with a paddle stirrer (5) and has a stainless steel headplate (6). A probe (7) is mounted on the headplate and projects into the fermentation vessel towards the layer of foam (4). The probe is connected via an electric circuit (8) to a pump (9) which is capable of pumping an antifoam substance through supply line (10) into the fermentation vessel (2). The fermentation vessel is earthed as shown at (11).

Figure 2:
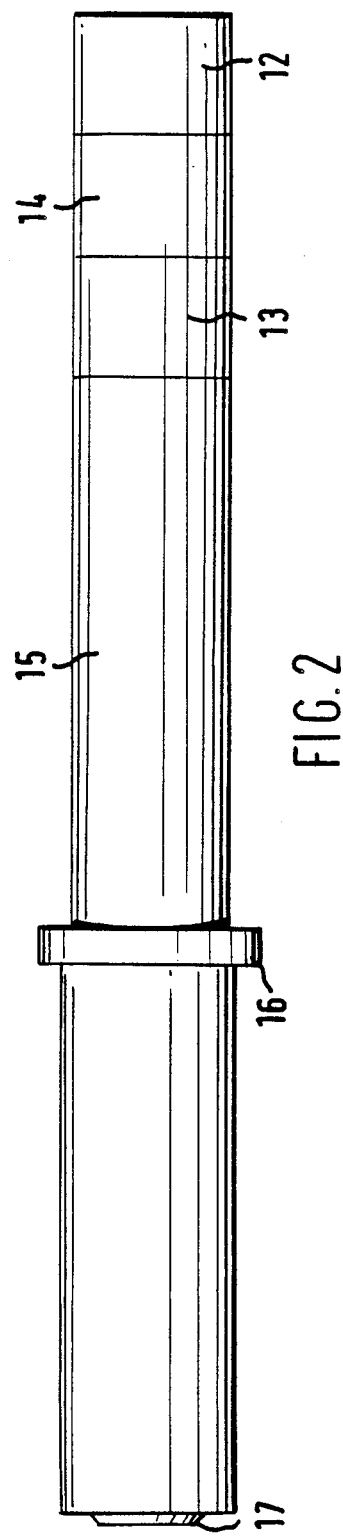
FIG. 2 shows a side view of the probe shown in FIG. 1.
Figure 3:
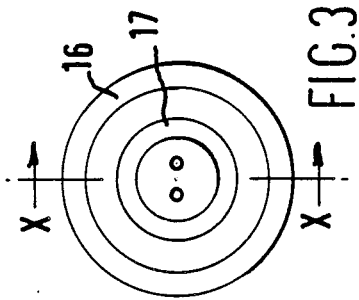
FIG. 3 shows a view of one end of the probe shown in FIG. 2.
Figure 4:
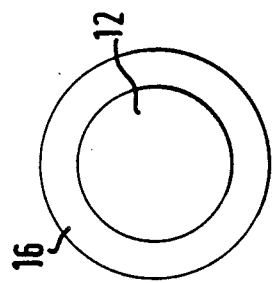
FIG. 4 shows a view of the other end of the probe shown in FIG. 2.
Figure 5:
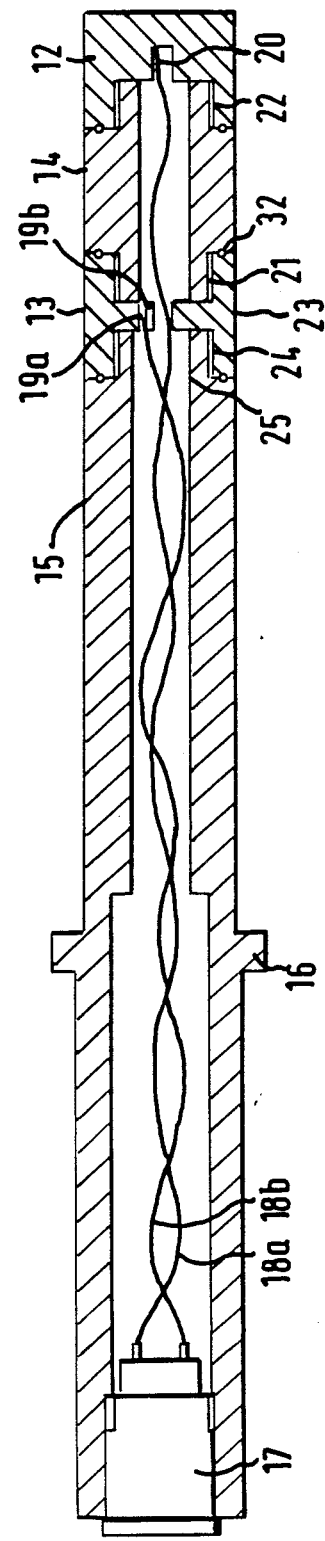
FIG. 5 shows a partial longitudinal section along the line X—X of the probe as shown in FIG. 3.

As shown more clearly in FIG. 2, the probe comprises a detecting electrode (12), a guard electrode (13), a first insulator (14) separating the detecting electrode from the guard electrode, and a second insulator (15), provided with a fermenter mounting flange (16), which is separated from the first insulator by the guard electrode. The second insulator is also provided with a socket (17) into which fits a plug (not shown). In use of the probe the plug is connected to the electric circuit (8), as shown in FIG 1. Two wires (18a and 18b) connect the socket to the electrodes.

As is apparent from FIGS. 2 to 5, the probe is of circular cross section, the electrodes and insulators being arranged along a common axis. It is assembled from five circularly cylindrical members which correspond to the two electrodes, the two insulators and the plug. The four members corresponding to the electrodes and insulators each have cooperating screw threads which enable them to be screwed together during assembly of the probe.

Thus the first insulator (14) is a circularly cylindrical body having two opposed, axially projecting screw threads (21 and 22) and an axial bore. It may be made of glass filled polytetrafluoroethylene. Preferably the first insulator (14) is made of polyetheretherketone.

The detecting electrode (12) is a circularly cylindrical body having a threaded recess which is adapted to receive the screw thread (22) of the first insulator. Centrally the recess continues as a small, axially-aligned cavity (20) which is the electric contact point for wire (18a) emanating from the socket (17). The detecting electrode is suitably made of stainless steel.

The guard electrode (13) is a circularly cylindrical body, suitably made of stainless steel. It has two opposed, threaded recesses (23 and 24) which communicate through a relatively narrow axial bore (19a) and a smaller bore (19b) adjacent to the axial bore (19a). The smaller bore is the electric contact point for wire (18b) emanating from the socket (17). The axial bore accomodates the wire connecting the detecting electrode to the socket. The first of the threaded recesses (23) is adapted to receive the screw thread (21) of the first insulator.

The second insulator (15) may be made from a single piece of glass-filled polytetrafluoroethylene, but is preferably made from a single piece of polyetheretherketone. The second insulator (15) has an axial bore and comprises three portions. The first portion is relatively long and narrow and has at one end an axially projecting screw thread (25) which is adapted to be received by the second of the threaded recesses (24) of the guard electrode. The second portion, which is relatively short and wide, constitutes the mounting flange (16). The third portion is relatively long and narrow and incorporates, at its free end, the socket (17).

In the assembled probe, the axial bores of the insulators and the guard electrode form a single cavity. Through this cavity run the two wires (18a and 18b) which connect the socket to the electric contact points (19a and 20) on the electrodes. The wires are suitably connected to the electric contact points by means of solder or silver loaded epoxy resin. 'O' rings (32) may be incorporated in the assembled probe to form a seal between the first insulator (14) and each of the detecting electrode (12) and the guard electrode (13), and between the second insulator (15) and the guard electrode (13). The 'O' rings, which may be made from any suitable sealing material, for example silicone, prevent the ingress of fluid into the probe.

The dimensions of the probe will depend upon the size of the fermentation vessel with which it is to be used. Typically a probe for use in a standard 3 litre fermenter will be about 12 cm long and 1.2 cm in diameter. The electrodes will typically be about 1 cm long and spaced about 1 cm apart.

Referring again to FIG. 1, the electric circuit (8) comprises a sub-circuit (26) for providing low alternating potential to the detecting electrode. This sub-circuit includes a resistor (27). The electric circuit further comprises a sub-circuit (28) for maintaining the guard electrode at the same potential as the detecting electrode. This sub-circuit includes a buffer amplifier (29). The electric circuit also comprises sub-circuit (30) for providing an electric signal to the antifoam supply regulator when rising foam causes a change in potential at the detecting electrode (12). This sub-circuit includes a comparator (31). Optionally the electric circuit also comprises a timer (32).

The probe together with the electric circuit constitute a sensor which is suitable for use with an antifoam regulator, such as the pump (9), in the control of foam build up in a fermenter. Together with an antifoam supply regulator, the apparatus constitutes a complete foam control system.

The method of using the probe will now be described with reference to FIG. 1.

As the level of the foam (4) in the fermentation vessel (2) rises, it will eventually touch the detecting electrode of the probe (7). When the foam touches the detecting electrode a current path is formed between the detecting electrode and earth (11). The resultant drop in potential at the detecting electrode is sensed by comparator (31). The comparator then activates a timer (not shown) which in turn activates a pump (9) for a preset time. A small quantity of antifoam is then supplied to the fermenter. This causes the foam to collapse.

The guard electrode of the probe is powered by the buffer amplifier (29) at all times at exactly the same potential as the detecting electrode. Consequently no electric field exists between the two electrodes, and hence no current may flow between them. The performance of the probe is therefore insensitive to an accumulation of material on the probe from the fermentation broth.

What is claimed:

1. A method of controlling the build up of foam in a fermentation vessel, which comprises supplying power to a detecting electrode positioned at a predetermined level in the fermentation vessel;

controlling the potential of a guard electrode positioned between the detecting electrode and the fermentation vessel such that a zero potential difference is maintained between the two electrodes; and supplying a controlled amount of an antifoam substance into the fermentation vessel whenever foam causes a change in potential at the detecting electrode.

2. A foam control system for use with a fermentation vessel comprising an antifoam supply regulator and a sensor, which sensor comprises a probe comprising a guard electrode, first and second insulators separated by the guard electrode, a detecting electrode separated from the guard electrode by the first insulator, means for independently connecting each of the electrodes to a power source, and vessel mounting means for positioning the detecting electrode at a predetermined level within the fermentation vessel with the guard electrode insulated from the vessel by the second insulator; and an electric circuit which comprises means for providing the detecting electrode with alternating potential, means for controlling the potential at the guard electrode so as to maintain a zero potential difference between the two electrodes, and means for providing the anitfoam supply regulator with an electric signal when foam causes a change in potential at the detecting electrode.

3. A foam control system as claimed in claim 2, in which the vessel mounting means comprises a flange or neck on the second insulator.

4. A foam control system as claimed in claim 2, in which the electrodes are composed of stainless steel.

5. A foam control system as claimed in claim 2, in which the insulators are composed of fiberglass loaded polytetrafluoroethylene, glass, polyetheretherketone or polyoxymethylene.

6. A foam control system as claimed in claim 5, in which the insulators are composed of polyetheretherketone.

7. A foam control system as claimed in claim 2 in which the electric circuit further comprises a timer which enables the electric circuit to provide the antifoam supply regulator with the electric signal for a preset time.

8. A fermenter comprising a foam control system as claimed in claim 2.

9. A foam control system, comprising:

a fermentation vessel;

an antifoam supply reservoir;

means including an antifoam supply regulator for supplying an antifoam substance to said vessel;

foam level sensor means in said vessel, said sensor means including a probe incorporating a guard electrode, first and second insulators separated by the guard electrode, a detecting electrode separated from the guard electrode by said first insulator, and vessel mounting means for positioning the detecting electrode of said probe at a predetermined level within the fermentation vessel with the guard electrode insulated from the vessel by the second insulator; and an electrical circuit including a source of alternating potential, means connecting said alternating potential to said detecting electrode and to said guard electrode and including means for controlling the potential at the guard electrode so as to maintain a zero potential difference between said guard and detecting electrodes, and circuit means responsive to a change in potential at said detecting electrode caused by foam reaching said predetermined level for supplying an electric signal to said antifoam supply regulator for operably controlling said regulator.

* * * * *